(12) United States Patent
Geist et al.

(10) Patent No.: US 9,999,444 B2
(45) Date of Patent: Jun. 19, 2018

(54) DEPTH CONTROLLED JAMSHIDI NEEDLE

(71) Applicant: Orthovita, Inc., Malvern, PA (US)

(72) Inventors: Wyatt Drake Geist, Davie, FL (US); Pierce Dalton Nunley, Shreveport, LA (US)

(73) Assignee: Orthovita, Inc., Malvern, PA (US)

( * ) Notice: Subject to any disclaimer, the term of this patent is extended or adjusted under 35 U.S.C. 154(b) by 274 days.

(21) Appl. No.: 13/956,067

(22) Filed: Jul. 31, 2013

(65) Prior Publication Data

US 2014/0039534 A1     Feb. 6, 2014

Related U.S. Application Data

(63) Continuation-in-part of application No. 13/409,483, filed on Mar. 1, 2012, now Pat. No. 8,758,383.
(Continued)

(51) Int. Cl.
    *A61B 17/34*         (2006.01)
    *A61B 90/00*         (2016.01)

(52) U.S. Cl.
CPC ...... *A61B 17/3472* (2013.01); *A61B 17/3494* (2013.01); *A61B 2090/034* (2016.02); *A61B 2090/062* (2016.02)

(58) Field of Classification Search
CPC . A61B 17/34; A61B 17/3403; A61B 17/3462; A61B 17/3472; A61B 17/3474; A61B 17/3494; A61B 10/02; A61B 10/0233; A61B 10/025; A61B 2010/0208; A61B 2019/304; A61B 2019/462
USPC ........................ 606/184, 185, 167–170, 172; 600/562–564, 566–567; 604/117, 264, 604/272, 274, 161–162, 164.01–164.12, 604/165.01, 165.02, 533–535
See application file for complete search history.

(56) References Cited

U.S. PATENT DOCUMENTS 3,750,667 A     8/1973    Pshenichny et al.
3,850,158 A     11/1974   Elias et al.
(Continued)

FOREIGN PATENT DOCUMENTS

| GB | 2403419 | 1/2005 |
|---|---|---|
| WO | 0217794 A1 | 3/2002 |
| WO | WO2010138895 | 12/2010 |

OTHER PUBLICATIONS

Latella et al., "Nanoindentation hardness. Young's modulus, and creep behavior of organic-inorganic silica-based sol-gel thin films on copper," J Mater Res 23(9): 2357-2365 (2008).
(Continued)

*Primary Examiner* — David C Eastwood
(74) *Attorney, Agent, or Firm* — Lerner, David, Littenberg, Krumholz & Mentlik, LLP

(57) ABSTRACT

A precision depth guided instrument, such as a Jamshidi needle, is provided for use in various surgeries related to the vertebrae. The instrument includes an outer cannula, an inner cannula and a stylet. After the cortical bone of a vertebra is penetrated by the outer cannula of the instrument, the depth of penetration of the inner cannula is adjusted by rotation of the inner cannula. The inner cannula is then moved further into the vertebrae, and a stop mounted on the outer cannula controls the depth of penetration of the inner cannula. The correct depth of penetration is determined by radiography prior to the procedure.

5 Claims, 21 Drawing Sheets

Related U.S. Application Data

(60) Provisional application No. 61/677,684, filed on Jul. 31, 2012, provisional application No. 61/448,030, filed on Mar. 1, 2011.

(56) References Cited

U.S. PATENT DOCUMENTS

| | | | |
|---|---|---|---|
| 4,142,517 A * | 3/1979 | Contreras Guerrero de Stavropoulos et al. | 600/567 |
| 4,262,676 A * | 4/1981 | Jamshidi | 600/566 |
| 4,469,109 A * | 9/1984 | Mehl | 600/566 |
| 4,793,363 A | 12/1988 | Ausherman et al. | |
| 4,838,282 A | 6/1989 | Strasser et al. | |
| 5,312,363 A * | 5/1994 | Ryan et al. | 604/167.04 |
| 5,368,046 A * | 11/1994 | Scarfone et al. | 600/567 |
| 5,372,583 A | 12/1994 | Roberts et al. | |
| 5,458,579 A | 10/1995 | Chodorow et al. | |
| 5,556,411 A | 9/1996 | Taoda et al. | |
| 5,660,186 A | 8/1997 | Bachir | |
| 5,693,031 A * | 12/1997 | Ryan et al. | 604/167.03 |
| 5,824,087 A | 10/1998 | Aspden et al. | |
| 6,019,776 A | 2/2000 | Preissman et al. | |
| 6,033,411 A | 3/2000 | Preissman | |
| 6,099,505 A * | 8/2000 | Ryan et al. | 604/167.04 |
| 6,248,110 B1 | 6/2001 | Reiley et al. | |
| 6,468,274 B1 * | 10/2002 | Alleyne | A61B 18/1206 604/114 |
| 6,468,279 B1 | 10/2002 | Reo | |
| 6,575,919 B1 | 6/2003 | Reiley et al. | |
| 6,582,441 B1 | 6/2003 | He et al. | |
| 6,749,595 B1 | 6/2004 | Murphy | |
| 7,081,122 B1 | 7/2006 | Reiley et al. | |
| 7,081,123 B2 | 7/2006 | Merboth et al. | |
| 7,153,306 B2 | 12/2006 | Ralph et al. | |
| 7,179,244 B2 | 2/2007 | Smith et al. | |
| 7,399,294 B2 | 7/2008 | Mickley | |
| 7,399,306 B2 | 7/2008 | Reiley et al. | |
| 7,678,077 B2 | 3/2010 | Harris et al. | |
| 7,722,567 B2 | 5/2010 | Tal | |
| 7,799,037 B1 | 9/2010 | He et al. | |
| 7,842,038 B2 | 11/2010 | Haddock et al. | |
| 7,850,651 B2 | 12/2010 | Allee et al. | |
| 7,905,884 B2 | 3/2011 | Simonton et al. | |
| 8,221,358 B2 | 7/2012 | McKay | |
| 8,257,358 B2 | 9/2012 | Haddock et al. | |
| 8,343,133 B2 | 1/2013 | Allee et al. | |
| 8,419,730 B2 | 4/2013 | Pellegrino et al. | |
| 8,608,702 B2 | 12/2013 | Beal et al. | |
| 8,758,383 B2 | 6/2014 | Geist | |
| 8,888,780 B2 | 11/2014 | Haddock et al. | |
| 2002/0169471 A1 | 11/2002 | Ferdinand | |
| 2003/0163062 A1 | 8/2003 | Bauer et al. | |
| 2003/0191414 A1 | 10/2003 | Reiley et al. | |
| 2003/0233114 A1 | 12/2003 | Merboth et al. | |
| 2004/0077973 A1 * | 4/2004 | Groenke et al. | 600/567 |
| 2005/0131345 A1 | 6/2005 | Miller | |
| 2005/0267383 A1 | 12/2005 | Groenke et al. | |
| 2006/0276747 A1 * | 12/2006 | Moos et al. | 604/117 |
| 2007/0010843 A1 | 1/2007 | Green | |
| 2007/0197935 A1 | 8/2007 | Reiley et al. | |
| 2007/0260184 A1 | 11/2007 | Justis et al. | |
| 2007/0260255 A1 | 11/2007 | Haddock et al. | |
| 2007/0265548 A1 * | 11/2007 | Goldenberg | 600/567 |
| 2009/0018468 A1 * | 1/2009 | Janssens | A61B 10/0266 600/567 |
| 2009/0187194 A1 | 7/2009 | Hamada | |
| 2009/0216260 A1 | 8/2009 | Souza et al. | |
| 2010/0069843 A1 | 3/2010 | Allee et al. | |
| 2010/0185161 A1 | 7/2010 | Pellegrino et al. | |
| 2012/0059321 A1 | 3/2012 | Hammond et al. | |

OTHER PUBLICATIONS

PCT/US2013/053038 International Search Report dated Oct. 29, 2013.
PCT/US2013/053038 Written Opinion of The International Searching Authority dated Jan. 31, 2015.

* cited by examiner

DEPTH CONTROLLED JAMSHIDI NEEDLE

CROSS REFERENCE TO RELATED APPLICATION

In accordance with 37 C.F.R. 1.76, a claim of priority is included in the Application Data Sheet filed concurrently herewith. Accordingly, the present application claims the benefit of the filing date of U.S. Provisional Application Ser. No. 61/677,684, filed Jul. 31, 2012, entitled "Depth Controlled Jamshidi Needle", this application is also a continuation-in-part of U.S. application Ser. No. 13/409,483, filed Mar. 1, 2012, entitled "Depth Controlled Jamshidi Needle" which claims priority under 35 U.S.C. 119(e) to U.S. Provisional Application Ser. No. 61/448,030, filed Mar. 1, 2011, entitled "Depth Controlled Jamshidi Needle", the contents of which are incorporated herein in their entirety.

FIELD OF THE INVENTION

The present invention relates to instruments employed for controlling accurate placement of devices, such as Jamshidi needles, used in spinal surgery. In particular, in addition to enabling a surgeon to accurately control the depth of needle penetration into the bone, the present device properly places dilation tubes for percutaneous surgical procedures.

BACKGROUND OF THE INVENTION

Medical procedures involving the vertebrae are normally complicated because of the preciseness and accuracy required to avoid both neural damage and injury to major blood vessels. Precision depth guided instruments are required to perform percutaneous spinal surgery. These surgeries sometimes require penetration of the hard cortical bone of the vertebra and traversal of the softer cancellous bone lying thereunder. A large force is normally required by the surgeon to penetrate the cortical bone. Once the cortical bone is penetrated, extreme care must then be taken to avoid rapidly penetrating through all of the cancellous bone. There is also the danger of rapidly passing through the cancellous bone and then through the cortical bone on the other side of the vertebra. This can result in injury or damage to the spinal cord and/or other organs or blood vessels located adjacent the spine. In some instances, the force required to penetrate the cortical bone is greater than a surgeon can apply by hand. In these instances a hammer or other similar instrument is required to force the instrument through the cortical bone. When a hammer or similar instrument is used, there is a greater danger of the instrument passing rapidly through the cancellous bone and out the other side of the vertebra. Preexisting conditions such as osteoporosis may complicate this problem.

DESCRIPTION OF THE PRIOR ART

U.S. Patent No. 5,458,579 discloses an apparatus for inserting a trocar/cannula assembly through a wall of an anatomical cavity of an individual. The apparatus includes a housing for holding the trocar/cannula assembly, a device for driving the trocar/cannula assembly into the individual, a spine, and a depth stop element mounted on the spine to control the depth which the trocar/cannula assembly is inserted into the individual.

U.S. Patent No. 6,033,411 discloses a depth guided instrument for use in performing percutaneous implantation of hard tissue implant materials. A depth guided stylet includes a point adapted for piercing hard tissue and self-tapping threads for self tapping into hard tissue. The instrument also includes a cannula surrounding the stylet which employs a pawl and rack of gear teeth to assist passing the cannula through the hard tissue.

U.S. Patent No. 7,678,077 discloses an instrument for injecting therapeutic and other agents into an individual at a target site. The instrument includes a catheter having a first elongate shaft and a second elongate shaft slidingly disposed within the first shaft. An indicator is secured to an end of the second elongate shaft and moves relative to a scale to indicate the position of the first and second shafts relative to their insertion into an individual.

None of the above noted prior art devices permit the operator of the device to adjust the depth of penetration of the Jamshidi needle or cannula based on information obtained from a patient prior to surgery. The depth of penetration can be adjusted depending on the point of entry into the body of the Jamshidi needle or cannula. In addition, none of these devices are constructed to place a tap tube or dilation tube simultaneously to placement of the needle.

SUMMARY OF THE INVENTION

A precision depth guided instrument, such as a Jamshidi needle, is provided for use in various surgeries related to the vertebrae. The instrument includes an outer cannula, an inner cannula and a stylet. After the cortical bone of a vertebra is penetrated by the outer cannula of the instrument, the depth of penetration of the inner cannula is adjusted by rotation of a stop mounted to the outer cannula. The inner cannula is then moved further into the vertebrae, and a stop mounted on the outer cannula controls the depth of penetration of the inner cannula. The correct depth of penetration is determined by radiography prior to and during the procedure. In at least one embodiment, the outer cannula is provided with at least one tap or dilation tube which may be placed within the patient for use in subsequent surgical operations after withdrawal of the jamshidi needle. The jamshidi needle may cooperate with the tap or dilation tubes to facilitate controlled withdrawal of the jamshidi from the cortical bone.

Accordingly, it is an objective of the instant invention to provide a depth controlled jamshidi needle which can be inserted into a patient to a precise location.

It is a further objective of the instant invention to provide a depth controlled jamshidi needle which can be inserted into a vertebra and then a portion of the device controllably moved to a precise location within the vertebra.

It is yet another objective of the instant invention to provide a depth controlled jamshidi needle which can be inserted into a vertebra a measured distance, the measured distance having been predetermined by radiography.

It is a still further objective of the invention to provide a depth controlled jamshidi needle which can be inserted into a vertebra an exact distance without any danger of exceeding the desired distance.

It is yet a further objective of the invention to provide a depth controlled jamshidi needle that includes at least one dilation tube positioned about the outer cannula which may be placed simultaneously with placement of the jamshidi needle.

It is still yet a further objective of the invention to provide a depth controlled jamshidi needle that includes at least one tap tube and at least one dilation tube positioned about the outer cannula which may be placed simultaneously with placement of the jamshidi needle.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof

DETAILED DESCRIPTION OF THE INVENTION

Figure 1:
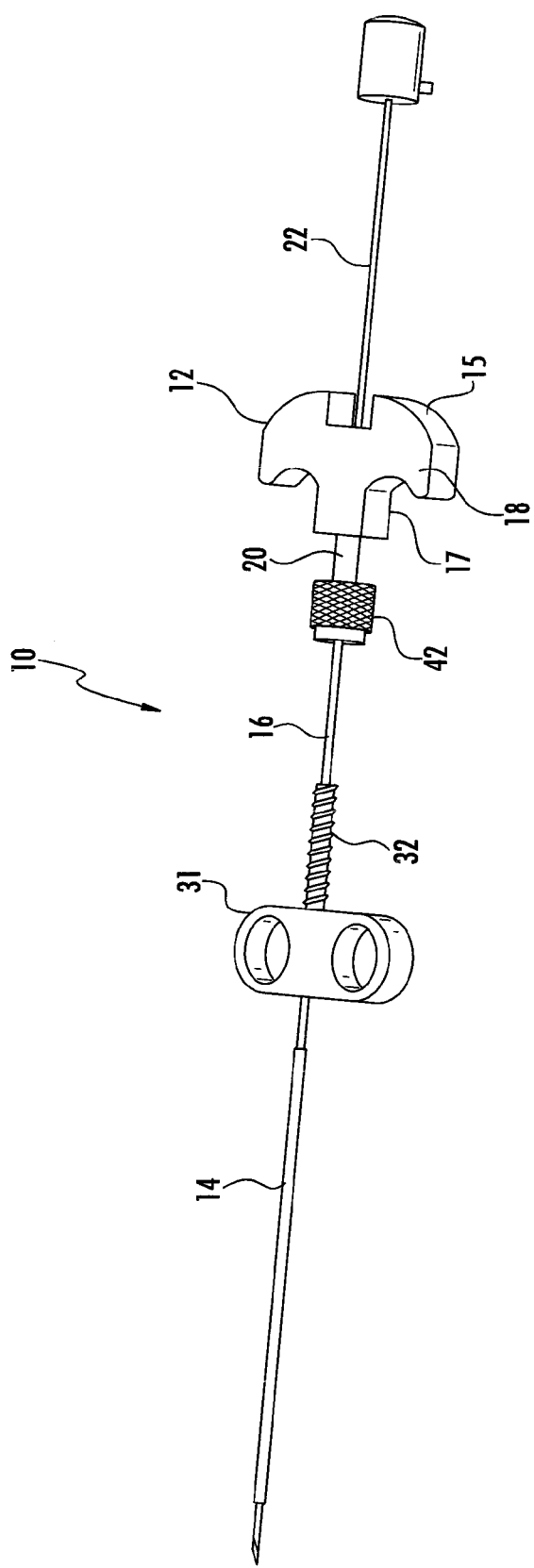
FIG. 1 is a perspective view of one embodiment of the present invention with the components partially exploded.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

FIGS. 1-11, which are now referenced, illustrate various embodiments of the present invention and the manner in which they are assembled. Like reference numerals refer to like components in the various figures. The needle depth controlled Jamshidi assembly 10 comprises a Jamshidi-type needle 12, and an outer cannula assembly 14. The Jamshidi-type needle 12 is slidably disposed within the outer cannula assembly 14. The Jamshidi-type needle 12 includes an inner cannula 16 which is secured to a handle 18. The handle 18 includes a collar or cylindrical portion 20. This cylindrical portion 20 is fixedly secured to the cannula 16. The handle 18 preferably has an ergonomic shape that can comfortably fit into a surgeon's or medical technician's hand. The handle includes an upper curved portion 15 which is shaped to conform to an individual's palm. The lower portion 17 of the handle 18 is also curved. The curve of the lower portion 17 of the handle is designed to be grasped by the fingers of an individual to assist in the control of the Jamshidi-type needle 12. The handle 18 is used to drive the cannula into, and sometimes through bones of a vertebra. Sometimes the Jamshidi-type needle 12 can be driven through the bone only by using pressure exerted by an individual's hand. Other times a hammer or other instrument must be employed to drive the needle 12 through a bone. There is a risk that, when a hammer or similar instrument is utilized, the Jamshidi-type needle 12 will pass too far into a vertebra. This can cause damage to nerves located nearby. Sometimes the needle passes completely through the vertebra and injures an adjacent blood vessel or internal organ. To prevent this, the present invention utilizes a second outer cannula 14 which is adjustably secured to the Jamshidi-type needle 12 to provide controlled linear traversal of the Jamshidi-type needle within the outer cannula assembly 14.

Figure 5:
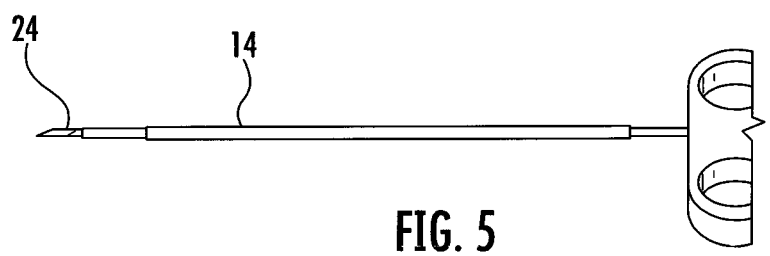
FIG. 5 is a partial view of the end portion of the embodiment illustrated in FIG. 3 illustrating the relationship of the two cannulae and needle.

A needle 22 is slidably positioned within the inner cannula 16 of the Jamshidi-type needle 12. The preferred embodiment of the present invention illustrates the needle 22 as having a conical tip 24 (FIGS. 5). However, other tips and needles can also be employed. For example, a trocar tip can be utilized. The tip 24 can be tapered, hollow, cannulated, etc. The tip can be utilized to extract a tissue sample. It can also be utilized to penetrate or anchor to a bone. In a preferred embodiment, the needle is detachable from the inner cannula so that a guidewire, Kirschner wire, K-wire or the like can be passed through the inner cannula to the surgical site. Alternatively, the Jamshidi needle can be removed and an orthopedic bone screw or other device can then be passed down the needle 22 and secured to the correct location on a bone. While the preferred embodiment of the present invention discloses a relatively rigid needle 22, other needles which are flexible can also be employed.

Figure 2:
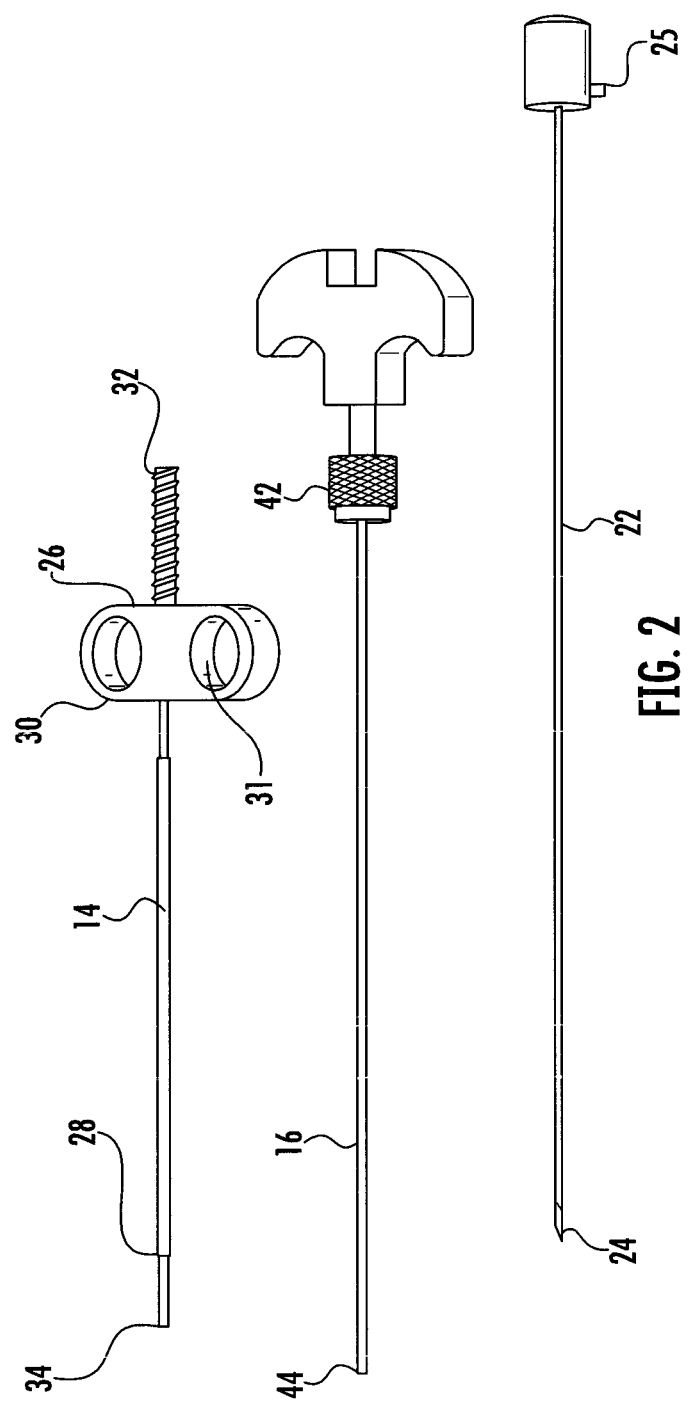
FIG. 2 is an exploded view of one embodiment of the present invention.

The outer cannula 14 comprises an upper portion 26 secured to a cannula 28 (FIG. 2). The upper portion 26 comprises a handle or grip 30 and a threaded sleeve 32. In the preferred embodiment of the outer cannula, the handle 30 and the threaded sleeve 32 are fixedly secured to each other. In other embodiments, these elements can be pivotably or removably secured to each other. The lower or second end 34 of the outer cannula 14 is constructed and arranged to penetrate and pass through bone. While the lower end 34 is normally a hollow tube with an end that tapers to a sharp edge, other edges can also be employed. For example, the edge can be serrated, saw toothed or sinusoidal.

The smooth edge is preferably utilized when the needle assembly is driven straight into or through a bone. The serrations or waves are employed when additional effort is required to penetrate a bone. The handle or grip 30 is preferably provided with apertures 31 into which a surgeon's fingers can be inserted to control the device.

Figure 7:
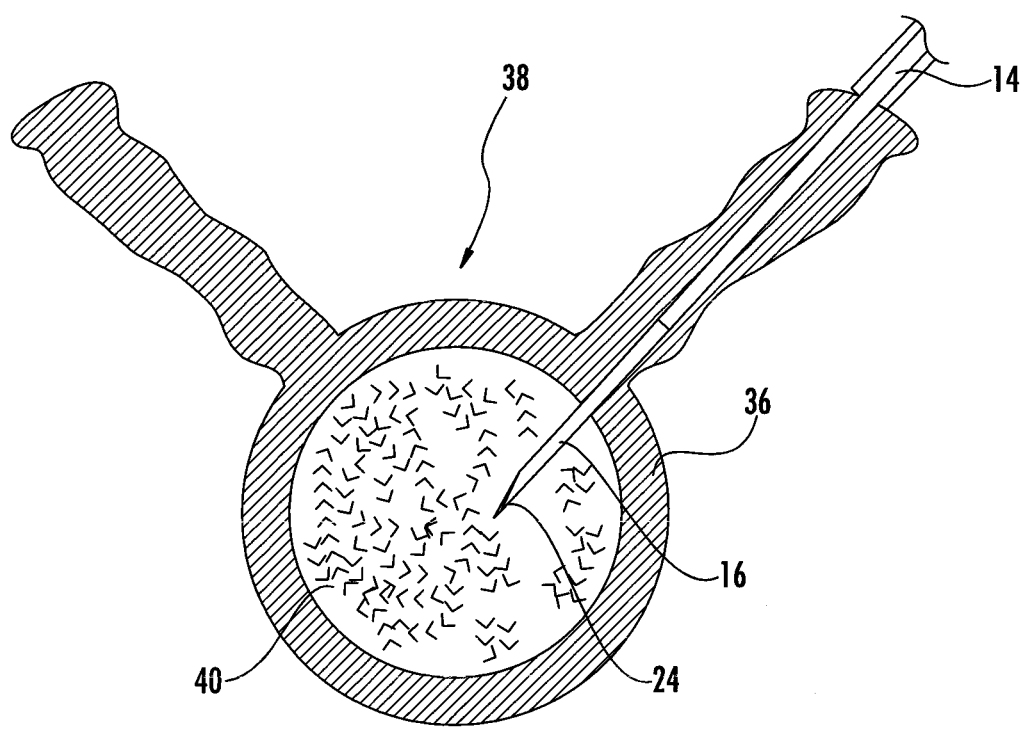
FIG. 7 is a cross sectional view of one embodiment of the present invention illustrated positioned in a vertebra.

FIG. 7 illustrates an example of one of the uses of the present invention. The outer cannula 14, the inner cannula 16 and the tip 24 of the needle 22 are passed through a cortical bone 36 of a vertebra 38 and into the cancellous bone 40. A sample of the cancellous bone may now be taken. In another situation, the needle 22 may be passed into the cortical bone 36 opposite the point of insertion into the vertebra. In these different situations it is very difficult for a surgeon or medical technician to judge the depth of penetration of the depth controlled Jamshidi type needle 10 into the vertebra. The remedy for this problem lies in the present invention. First, a radiography image of the vertebra being operated upon is taken. Next, the depth into the vertebra that the surgeon wants the needle to penetrate is measured or estimated. The outer cannula includes a first stop member 28. The outer cannula is driven into the bone until the first stop member 28 contacts the top surface of the bone, providing a reference depth that the outer cannula has penetrated the bone. The Jamshidi-type needle 12 of the present invention includes a threaded nut 42 or similar device which is rotatably secured to the cannula 16 by a bearing. The threads on the nut 42 match the threads on the sleeve 32. After the surgeon inserts the needle into a patient and through the cortical bone 36 of a vertebra, the cannula 16 is inserted further into the vertebra by rotating the nut 42. Rotation of the nut 42 moves the cannula and needle 22 further into the vertebra. The distance that these elements are moved can be measured along the threaded sleeve. Alternatively, since the threads have a fixed pitch, the surgeon need only count the rotations of the nut or inner cannula to determine the traversal of the inner cannula through the outer cannula and into the bone. The distance the needle needs to travel into the vertebra, which has been determined by radiography, can be accurately determined. Preferably, marks or indicia are placed on sleeve 32 which allow the surgeon to visually determine the position of the inner cannula with respect to the outer cannula. The surgeon or medical technician can now rotate the nut 42 until it reaches the desired mark of indicia on sleeve 32. At this point, the cannula 16 and needle 22 are now exactly where they need to be positioned. The nut can be rotated by hand or with a wrench or similar device. The wrench may be utilized if a relatively hard bone is to be penetrated by the device. Because the first stop member 28 is placed a predetermined distance from the distal tip of the outer cannula, the surgeon has a precise knowledge of how far the bone has been penetrated.

In an alternate embodiment, the nut 42 is fixedly secured to the collar 20 and handle or grip 30. In this embodiment the handle 30 is rotated, which in turn rotates the collar 20 and nut 42. This moves the cannula 16 further into the vertebra until the desired position is reached. Rotation of the handle 30 permits additional torque to be applied to the nut 42, and in certain instances does not required the use of a wrench or similar tool.

Figure 3:
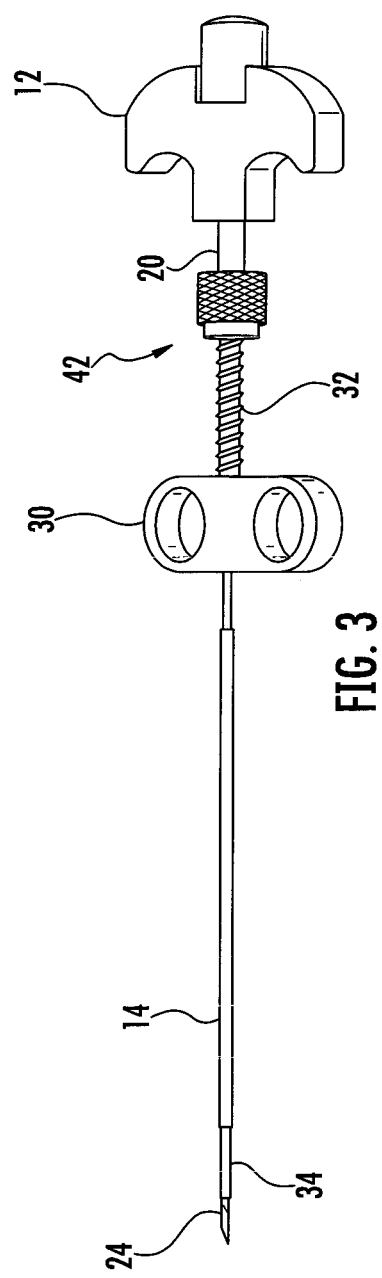
FIG. 3 is a perspective view of one embodiment of the present invention illustrated with a component placement prior to insertion into a patient.
Figure 4:
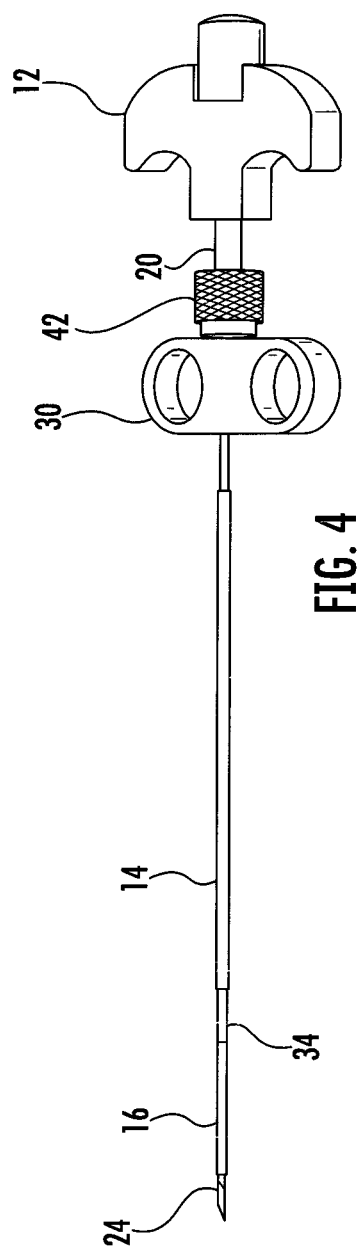
FIG. 4 is a perspective view of one embodiment of the present invention illustrated with an inner cannula moved to position for penetration further into a vertebra.

FIG. 3 illustrates the position of the elements of the invention prior to rotation of nut 42. The end of cannula 16 is adjacent the end 34 of the outer cannula. The tip 24 of the needle 22 protrudes slightly past this point. As illustrated in FIG. 4, after nut 42 is rotated, the inner cannula 16 and needle 22 move past the end 34 of cannula 14. The distance that the inner cannula 16 and needle need to move past the end 34 of cannula 14 has been previously determined by radiography. The end 44 (FIG. 2) of inner cannula 16 can be similar in construction to end 34 of outer cannula 14. While the end 44 is normally a hollow tube with an end that tapers to a sharp edge, other edges can also be employed. For example, the edge can be serrated, saw toothed or sinusoidal. The smooth edge is preferably utilized when the needle assembly is driven straight into or through a bone. The serrations or waves are employed when additional effort is required to penetrate a bone.

Figure 6:
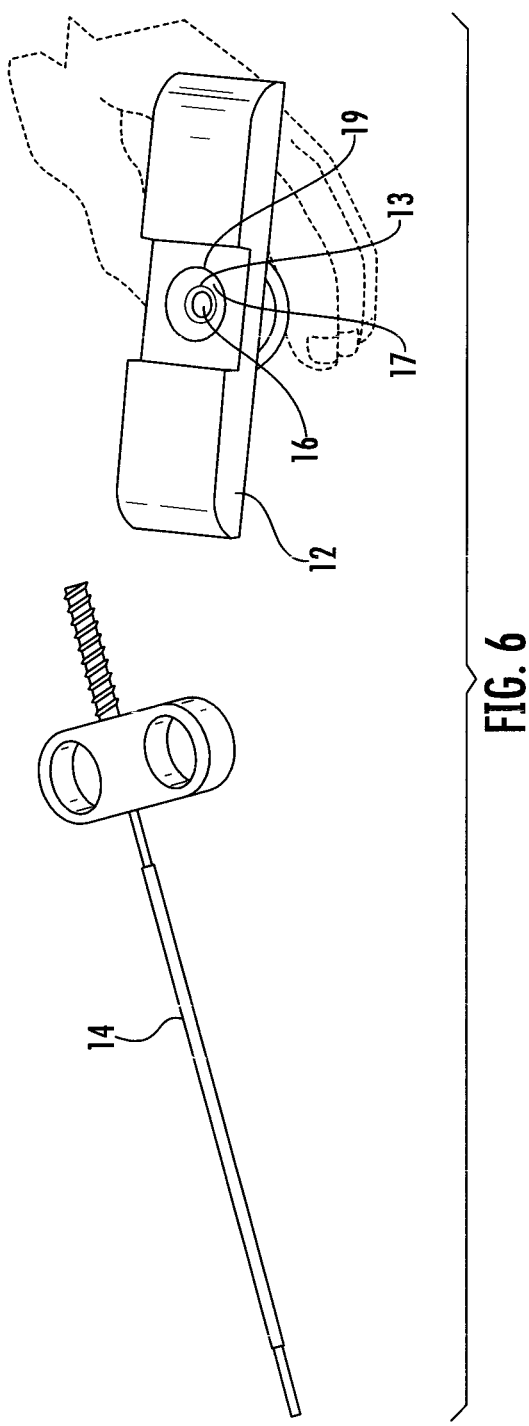
FIG. 6 is a top view of a handle of the inner cannula into which a needle is inserted, illustrated with a perspective view of the outer cannula.

FIG. 6 illustrates the hollow cannula 16 into which the needle 22 is slidably located. Also visible in FIG. 6 is funnel 17 which extends from the upper portion 15 of handle 18 to the first end 13 of the inner cannula 16. The funnel 17 includes an open mouth 19 which tapers substantially to the diameter of the inner bore of the inner cannula. The funnel provides the user with an easily targeted aperture for insertion of the needle 22 or a guidewire, also known as a Kirschner wire (not shown) often used in spinal as well as other types of surgeries.

Figure 11:
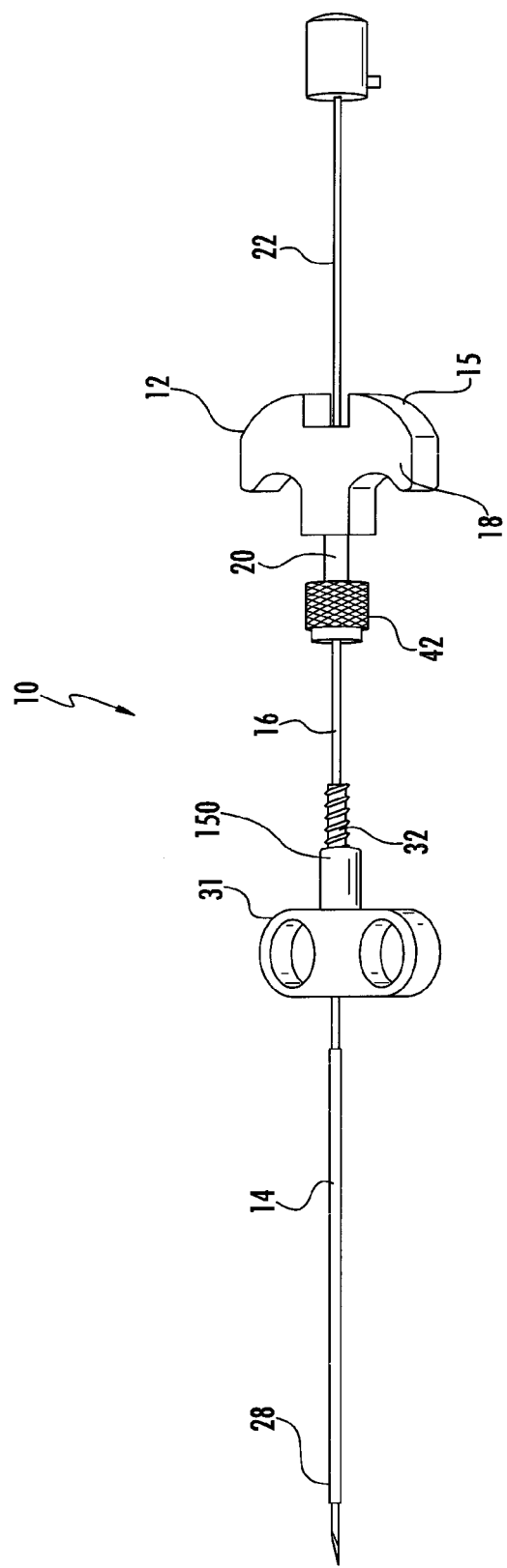
FIG. 11 is a perspective view of the invention illustrated in FIG. 1 including an optional hard stop.
Figure 12:
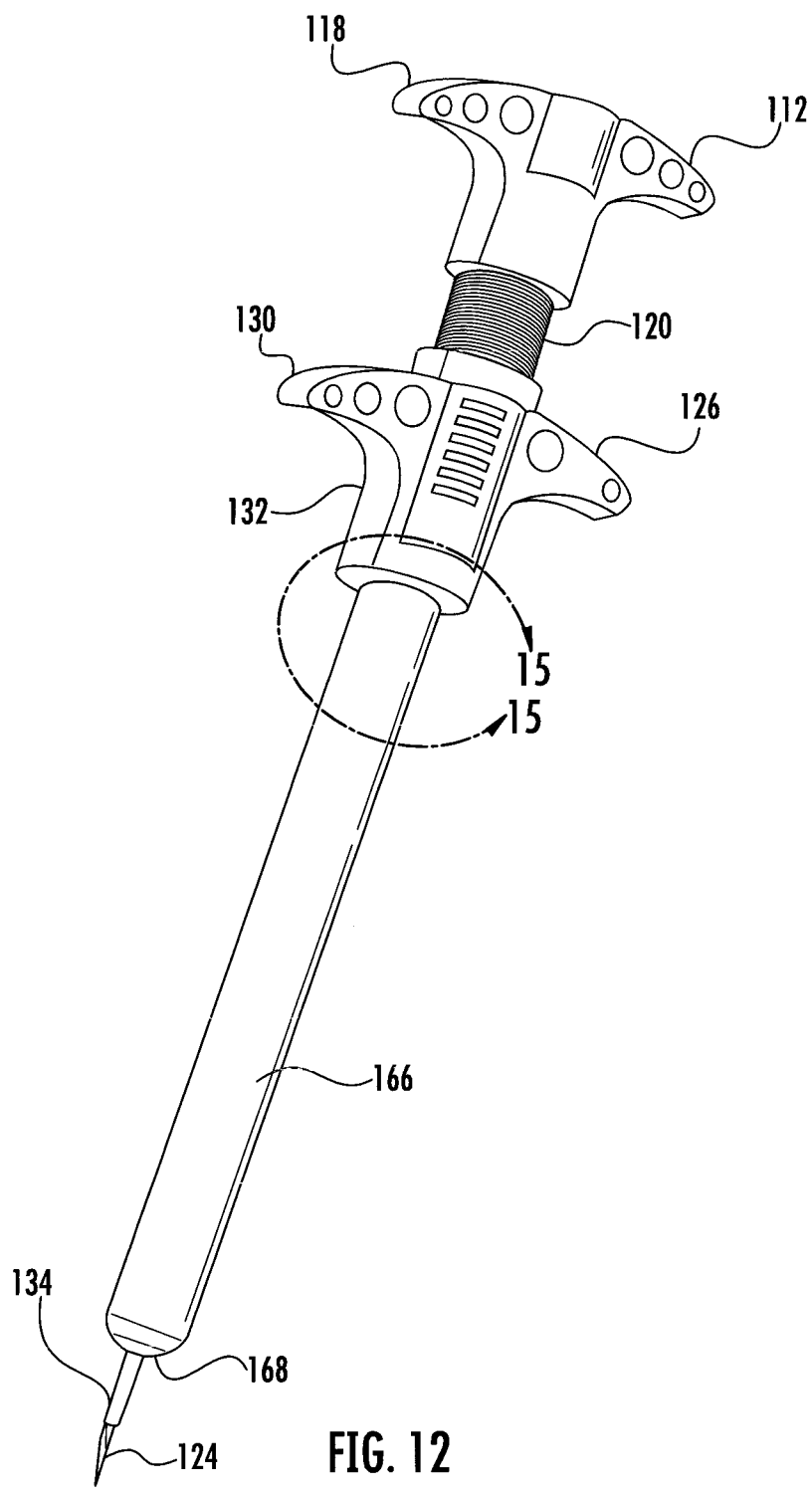
FIG. 12 is a perspective view of one embodiment of the present invention illustrated with a tap tube and a dilation tube positioned about the outer cannula.
Figure 13:
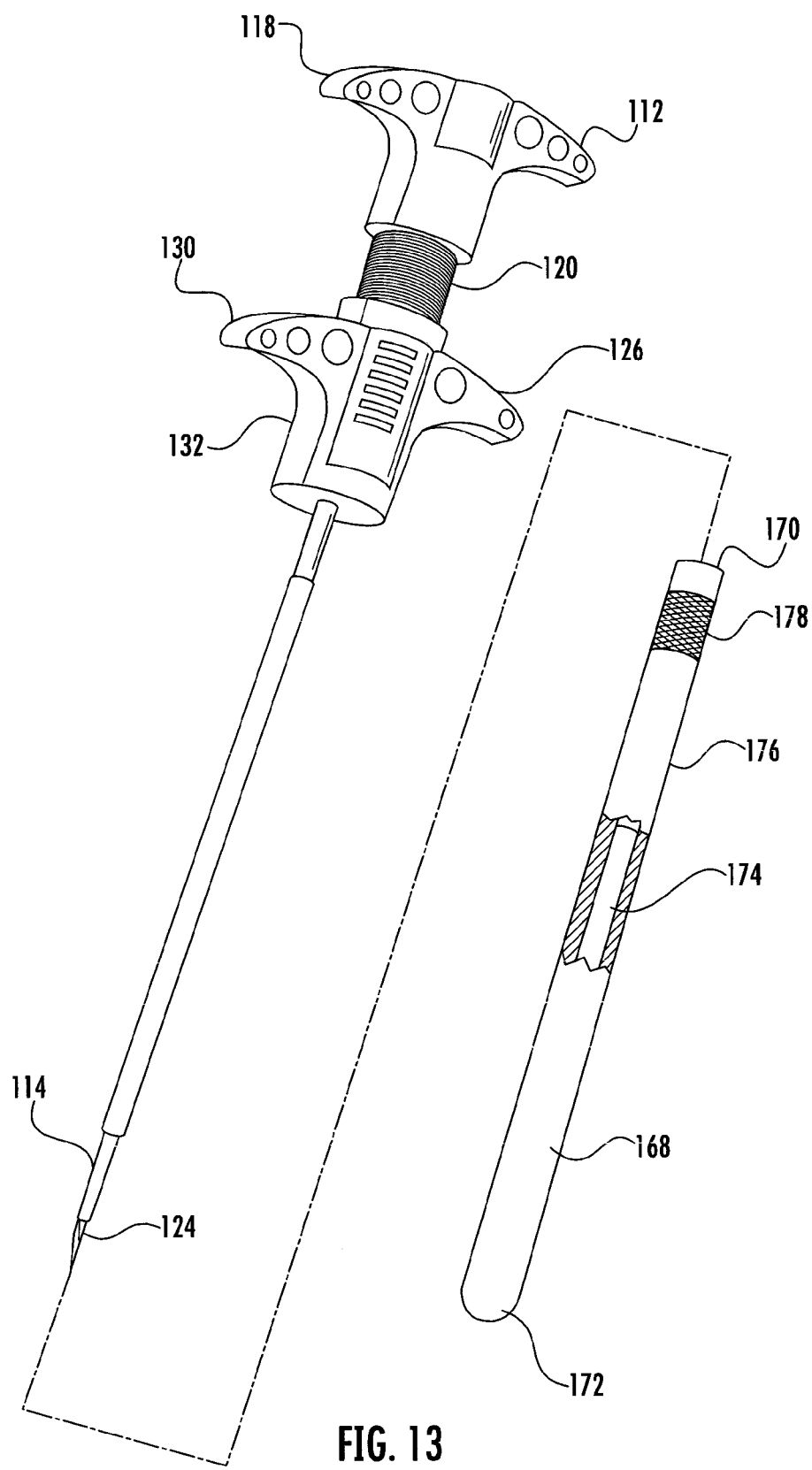
FIG. 13 is a perspective partially exploded view of one embodiment of the present invention illustrating the tap tube partially in section.
Figure 14:
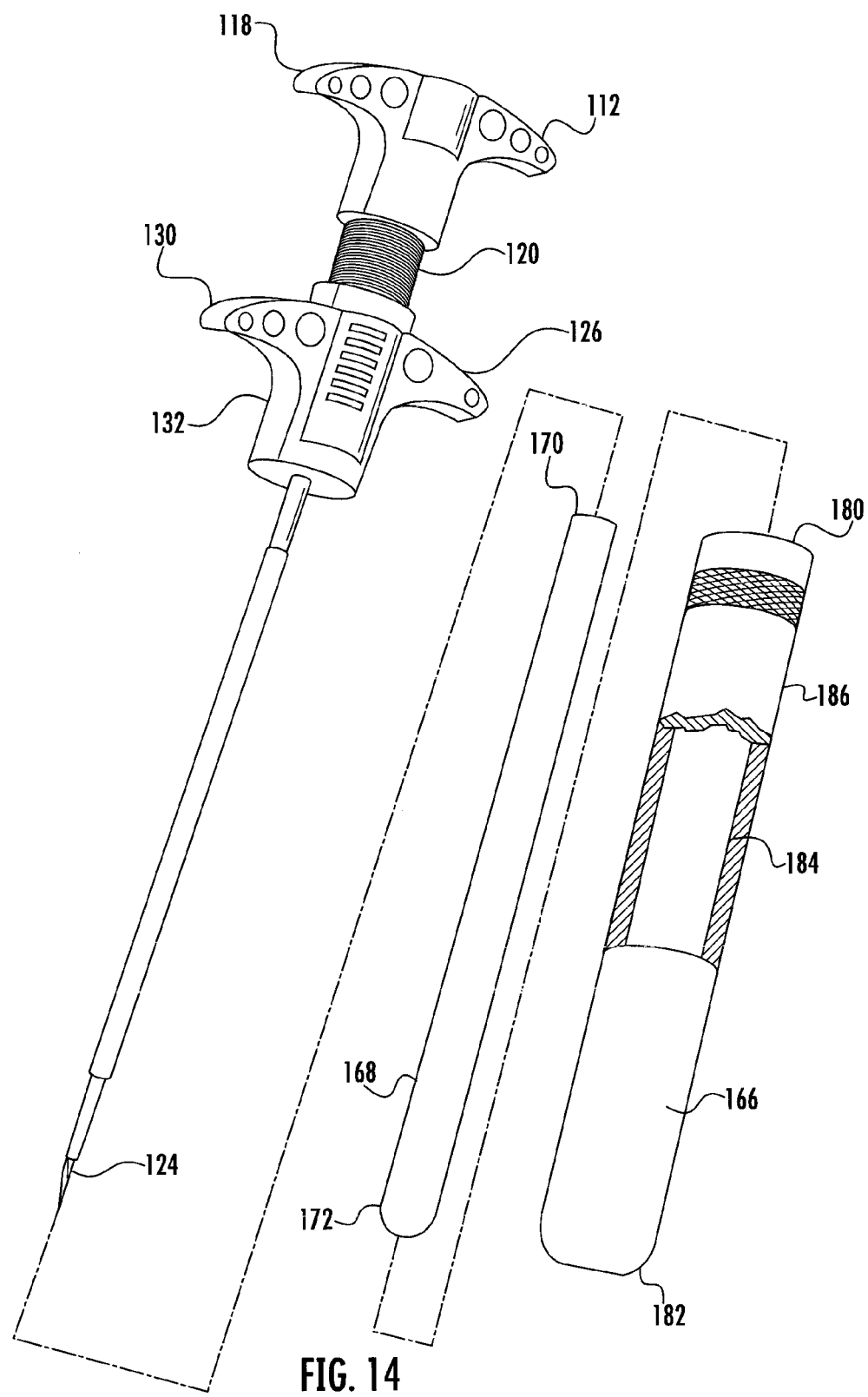
FIG. 14 is a perspective partially exploded view of the embodiment of FIG. 12 illustrating the tap tube and dilation tube partially in section.

FIG. 11 illustrates an optional collar or spacer 150 that can be placed on the sleeve 32. This spacer or collar 150 enables the surgeon or medical technician to precisely place the cannula 16 and needle 22 within a bone or other portion of a patient. The precise desired location of the cannula 16 and needle 22 is first determined by radiography. A measurement of this location is taken, and then a spacer or collar 150 is selected; the length of the spacer corresponding to this measurement. The spacer or collar is then placed over the sleeve 32 and the procedure is performed. The first stop member 28 determines the depth that the outer cannula 14 enters the bone and the inner cannula or nut 16, 42 is rotated to position the distal end of the needle 22 precisely where the surgeon or medical technician has determined it should be. This optional spacer prevents any over-insertion of the cannula 16 and needle 22.

Figure 8:
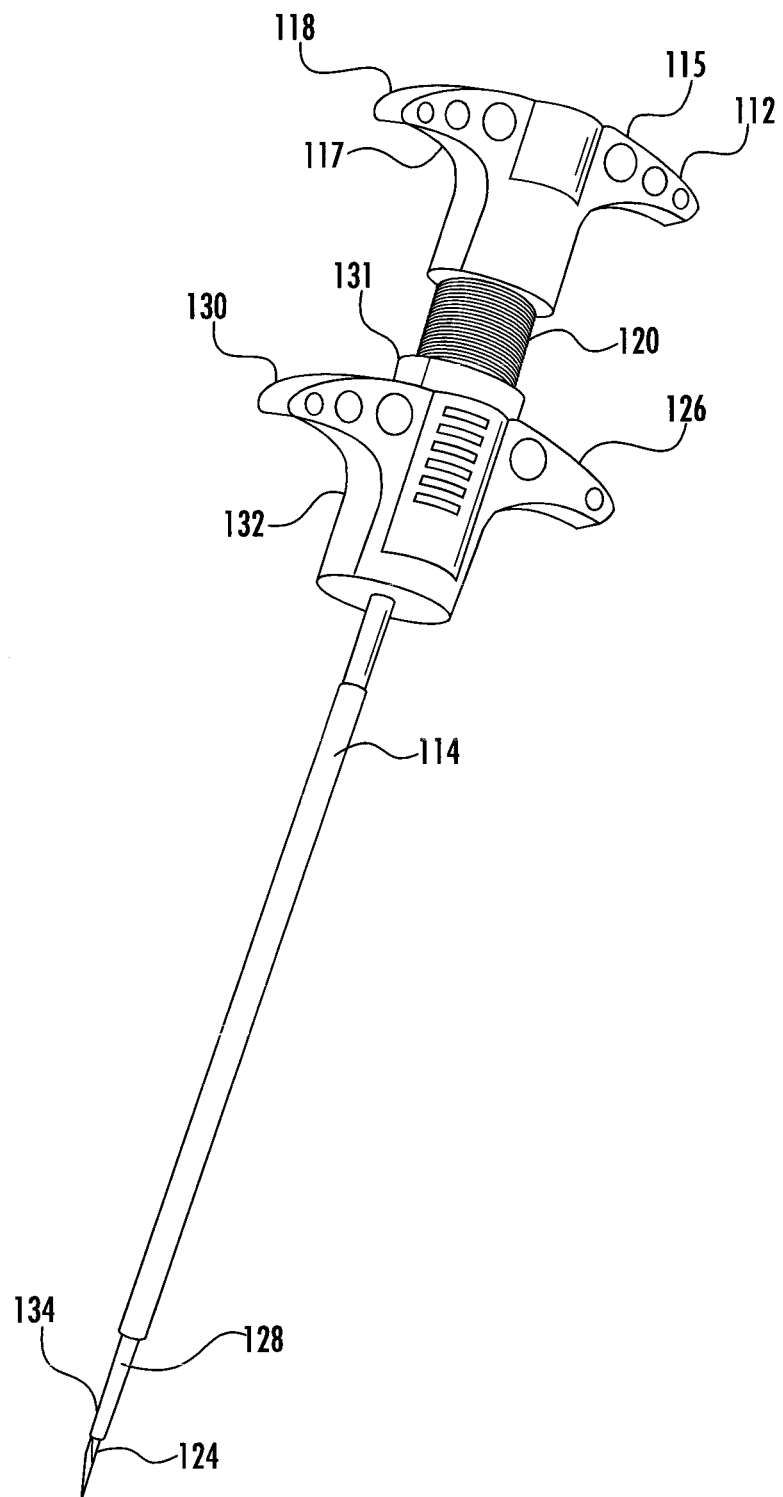
FIG. 8 is a perspective view of one embodiment of the present invention illustrated in a position similar to FIG. 3.
Figure 9:
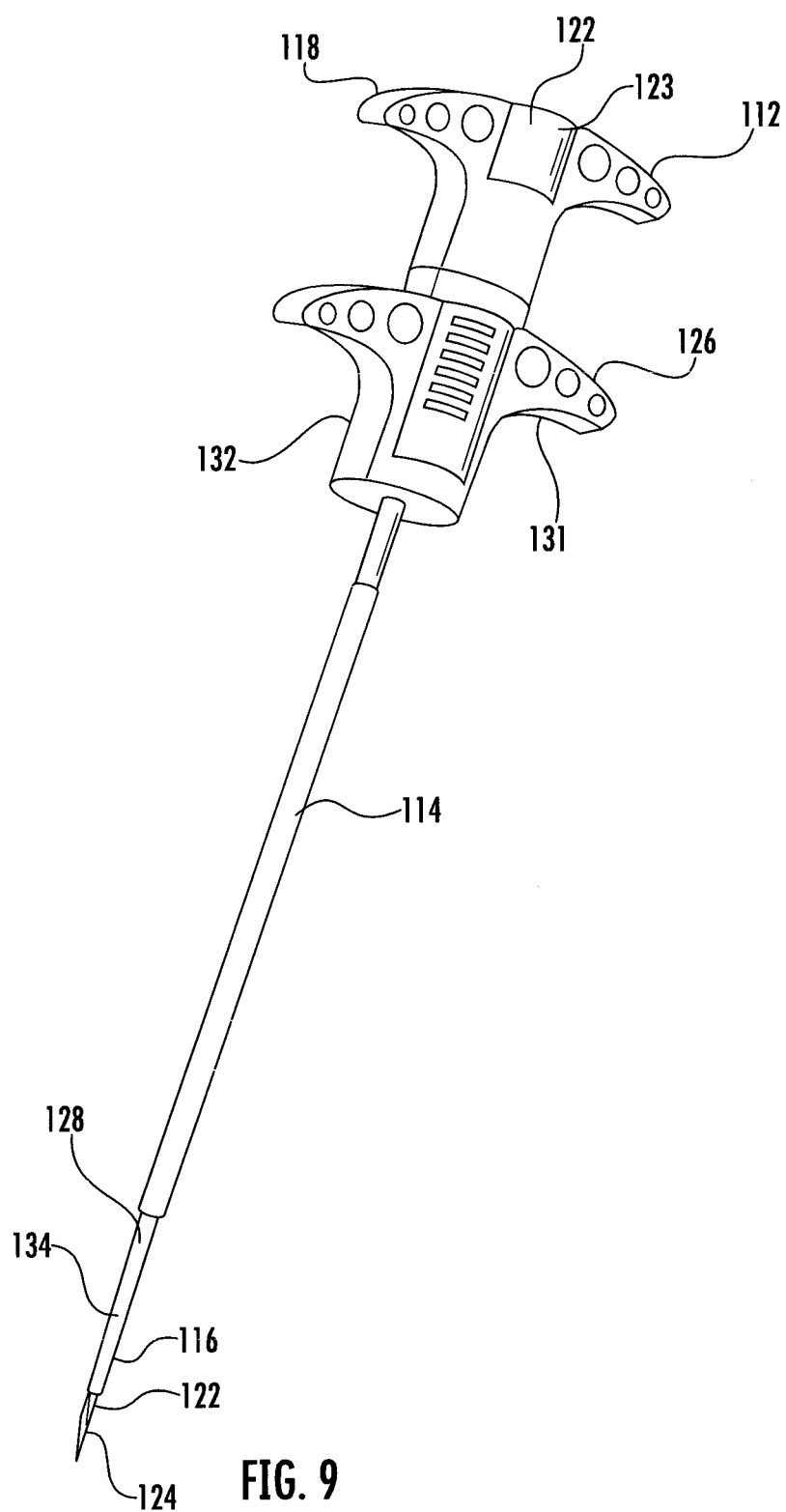
FIG. 9 is a perspective view of one embodiment of the present invention illustrated in a position similar to FIG. 4.
Figure 10:
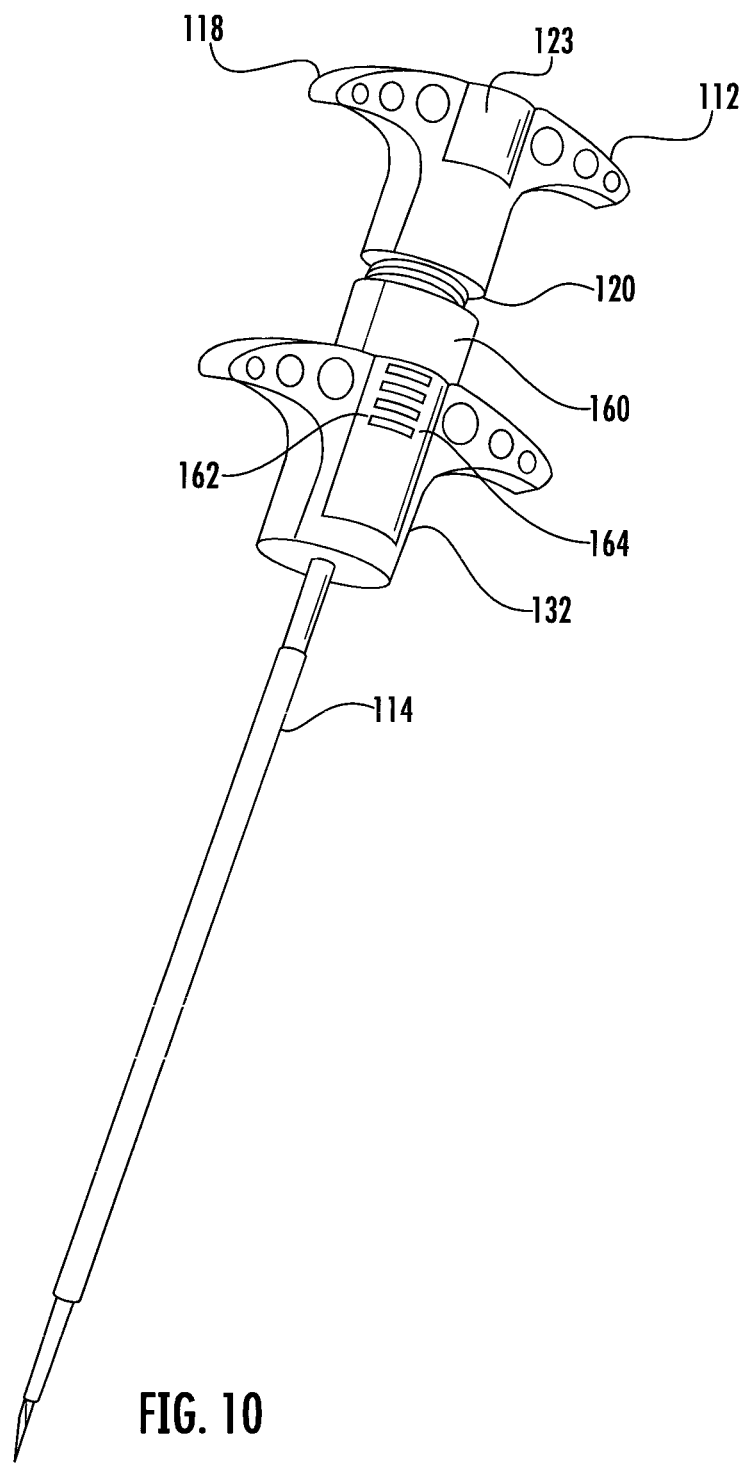
FIG. 10 is a perspective view of one embodiment of the present invention illustrated with an optional hard stop.

FIGS. 8-10 illustrate an alternate embodiment of the present invention. In these figures, a Jamshidi-type assembly 112 is slidably disposed within an outer cannula assembly 114. The Janshidi-type needle 112 includes a cannula 116 which is secured to a handle 118. The handle 118 includes a threaded collar portion 120. This threaded collar portion 120 is fixedly secured or molded to the handle 118. The handle 118 preferably has an ergonomic shape that can comfortably fit into a surgeon's or medical technician's hand. The handle includes an upper curved portion 115 which is shaped to conform to an individual's palm. The lower portion 117 of the handle 118 is also curved. The curve of the lower portion 117 of the handle is designed to be grasped by the fingers of an individual to assist in the control of the Jamshidi-type assembly 112. The handle 118 is used to drive the cannula into, and sometimes through bones of a vertebra. Sometimes the Jamshidi-type assembly 112 can be driven through the bone only by using pressure exerted by an individual's hand. Other times a hammer or other instrument must be employed to drive the Jamshidi-type assembly 112 through a bone. There is a risk, that when a hammer or similar instrument is utilized, the Jamshidi-type assembly 112 will pass too far into a vertebra. This can cause damage to nerves located nearby. Sometimes the needle passes completely through the vertebra and injures an adjacent blood vessel or internal organ. To prevent this, the present invention utilizes a second cannula 114 which is adjustably secured to the Jamshidi-type assembly 112.

A needle 122 is slidably positioned within the cannula 116. The needle, like the other embodiments includes an enlarged head member 123 which includes a boss 25 (FIG. 2) or the like suitable to secure the needle within the inner cannula assembly. In a most preferred embodiment, the boss cooperates with the handle 118 to function as a bayonet type mount. This embodiment of the present invention illustrates the needle as having a conical tip 124, however, other tips and needles can also be employed. For example, a trocar needle can be utilized. The tip 124 can be tapered, hollow, etc. The tip can be utilized to extract a tissue sample. It can also be utilized to anchor the needle to a bone. An orthopedic bone screw or other device can then be passed down the needle and secured to the correct location on a bone. While the preferred embodiment of the present invention discloses a relatively rigid needle, other needles which are flexible can also be employed. Alternatively, the bayonet mount may be utilized to remove the needle from the inner cannula for placement of a guidewire, K-wire or a Kirschner wire.

The outer cannula 114 comprises an upper portion 126 secured to a cannula 128 (FIG. 8). The upper portion 126 comprises a handle or grip 130. In this embodiment, the outer or second cannula 114 and the handle 130 are fixedly secured to each other. In other embodiments, these elements can be pivotably secured to each other. The lower end 134 of the outer cannula 114 is constructed and arranged to penetrate and pass through bone. While the end 134 is normally a hollow tube with an end that tapers to a sharp edge, other edges can also be employed. For example, the edge can be serrated, saw toothed or sinusoidal. The smooth edge is preferably utilized when the needle assembly is driven straight into or through a bone. The serrations or waves are employed when additional effort is required to penetrate a bone.

The Jamshidi-type assembly 112 of this embodiment includes a threaded collar portion 120. The second cannula 114 includes a housing 132 at a top end thereof. The housing is relatively hollow and includes threads which match the threads on sleeve portion 120. After the surgeon inserts the needle into a patient and through the cortical bone 36 of a vertebra, the cannula 116 is inserted further into the vertebra by rotating the handle 118 and sleeve portion 120. Rotation of sleeve 120 moves the cannula 116 and needle further into the vertebra. The distance that these elements are moved can be measured along the sleeve portion 120 which is provided with windows 162 and/or indicia 164. The distance the needle needs to travel into the vertebra, which has been determined by radiography, will be measured along sleeve portion 120. The surgeon or medical technician can now rotate handle 118 and sleeve 120 until it reaches the desired mark of indicia on sleeve 120. At this point, the cannula 116 and Jamshidi-type assembly 112 are now exactly where they need to be positioned.

FIG. 10 illustrates an optional collar or spacer 160 that can be placed on the sleeve 120. This spacer or collar 160 enables the surgeon or medical technician to precisely place the cannula 116 and Jamshidi-type assembly 112 within a bone or other portion of a patient. The precise desired location of the cannula 116 and Jamshidi-type assembly 112 is first determined by radiography. A measurement is taken and then a spacer or collar 160 is selected which corresponds to this measurement. The spacer or collar is then placed over the sleeve 120 and the procedure is performed. This optional spacer prevents any over-insertion of the cannula 116 and Jamshidi-type assembly 112.

Figure 15:
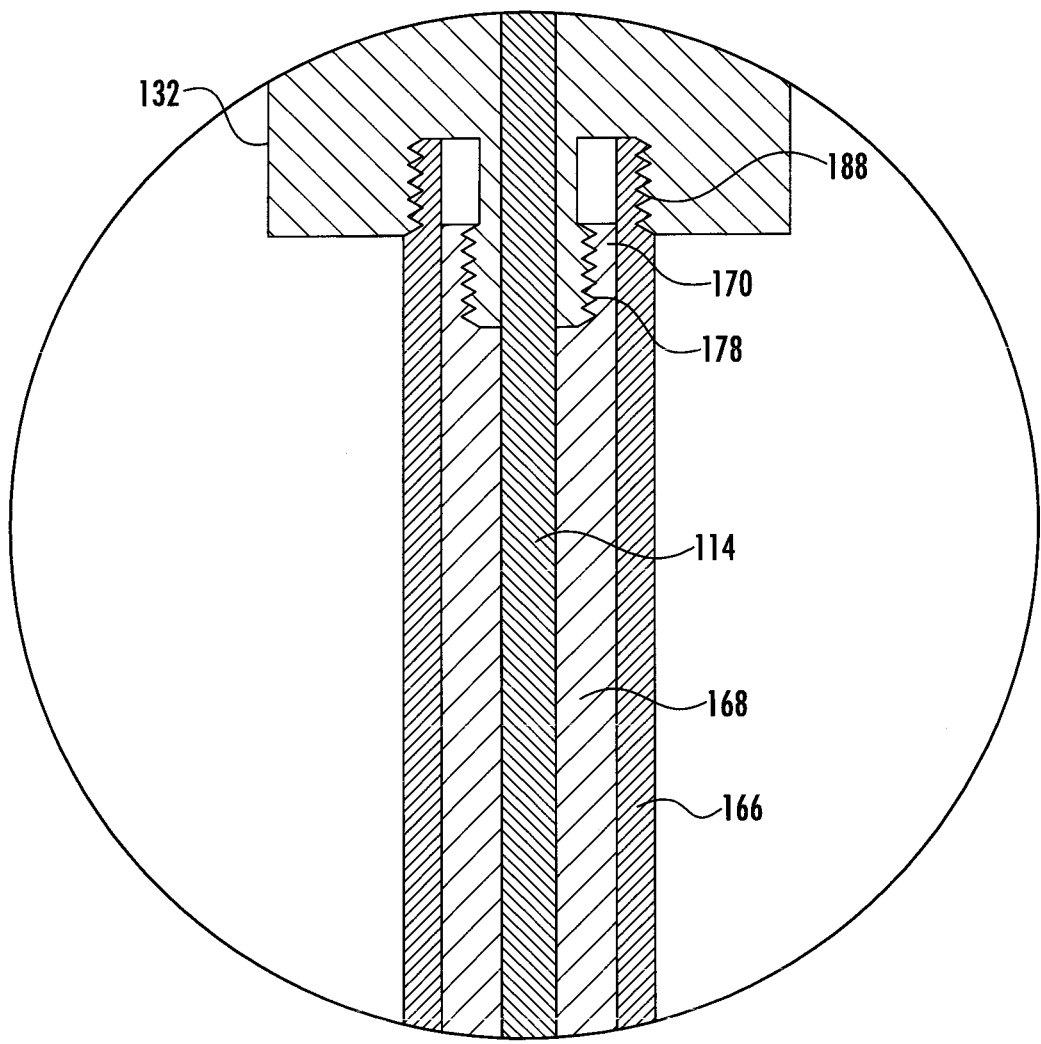
FIG. 15 is a partial section view taken along lines 15-15 of FIG. 12 illustrating connection between the tap and dilation tubes and the outer cannula.
Figure 16:
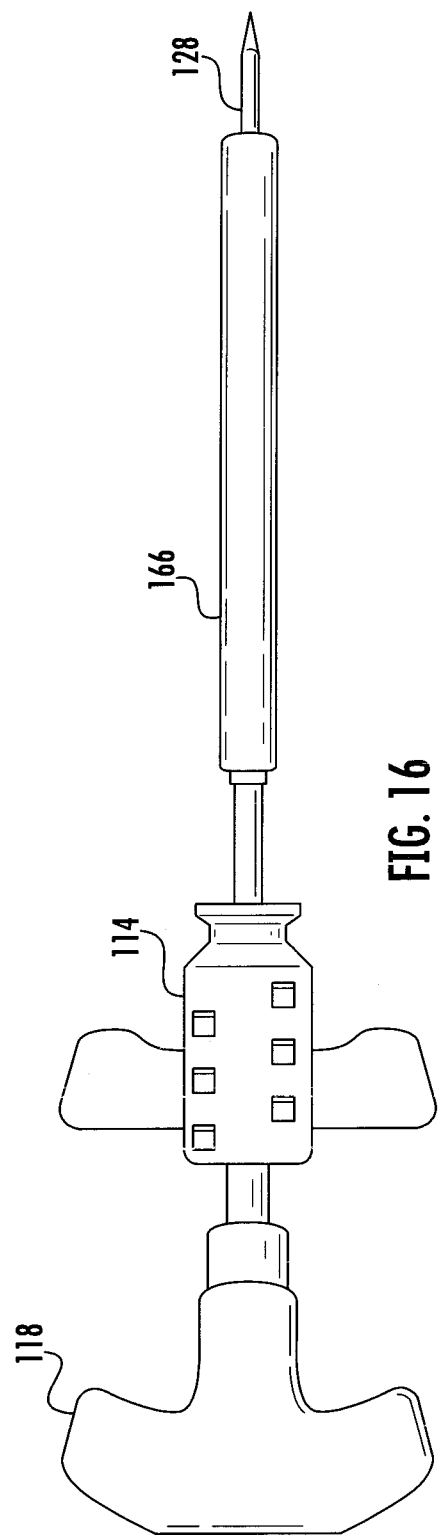
FIG. 16 is a perspective view of one embodiment of the present invention illustrated with the tap tube positioned about the outer cannula.
Figure 17:
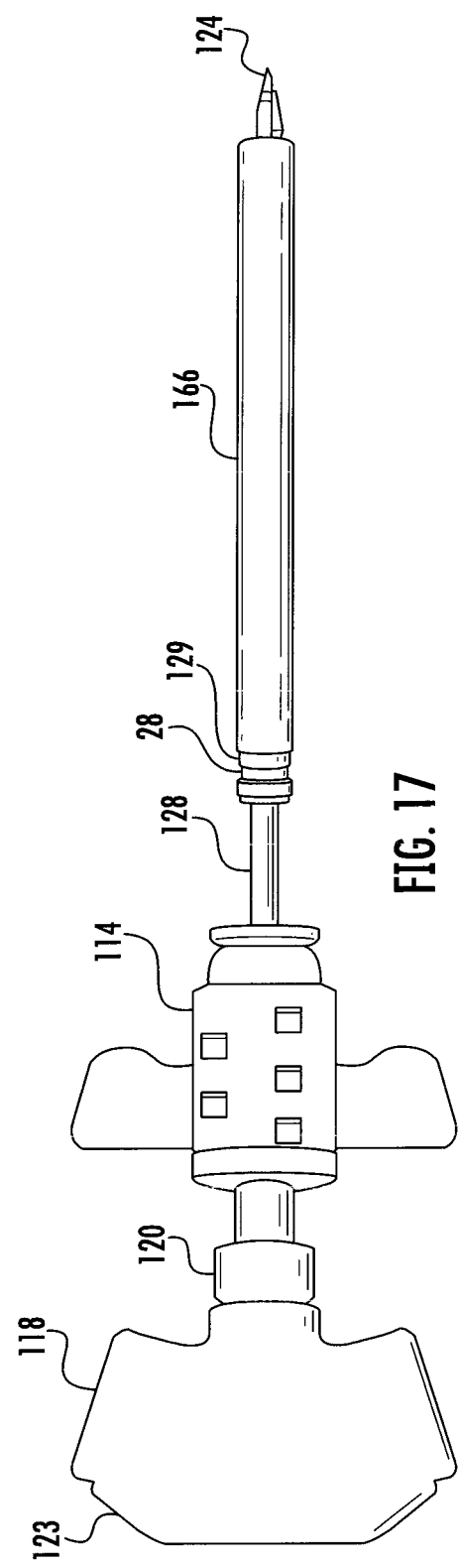
FIG. 17 is a perspective view of the embodiment shown in FIG. 16 illustrating partial removal of the outer cannula from the tap tube.
Figure 18:
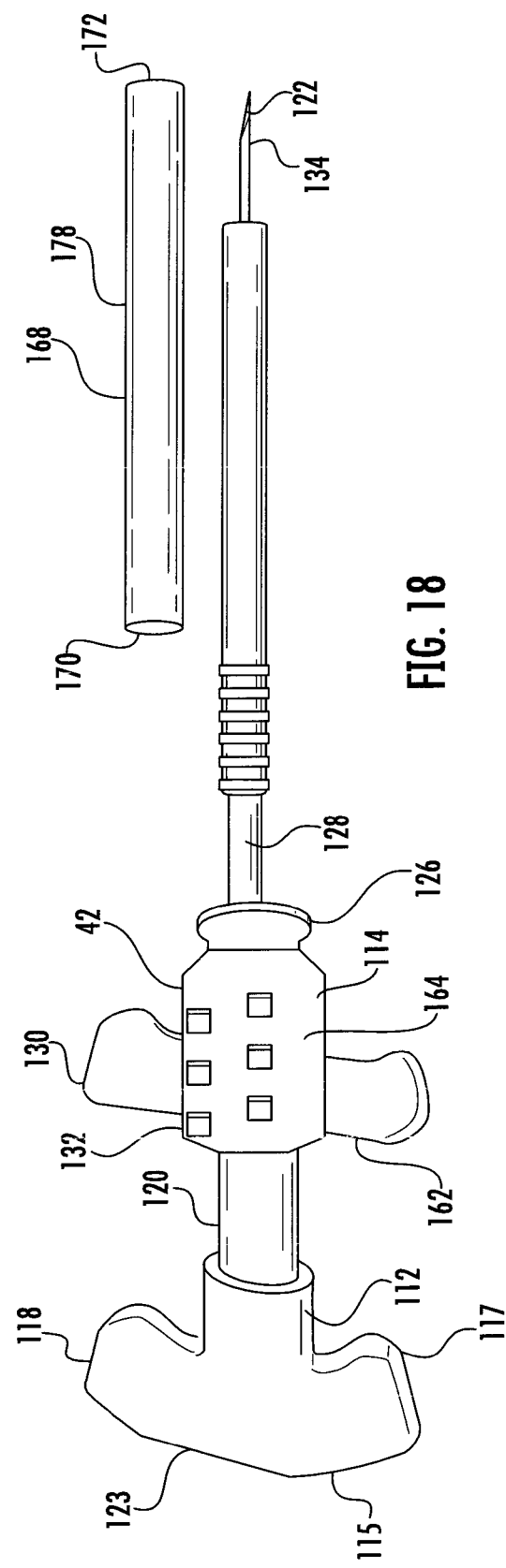
FIG. 18 is a perspective view of the embodiment illustrated in FIG. 16 illustrated with the tap tube removed from the outer cannula.
Figure 19:
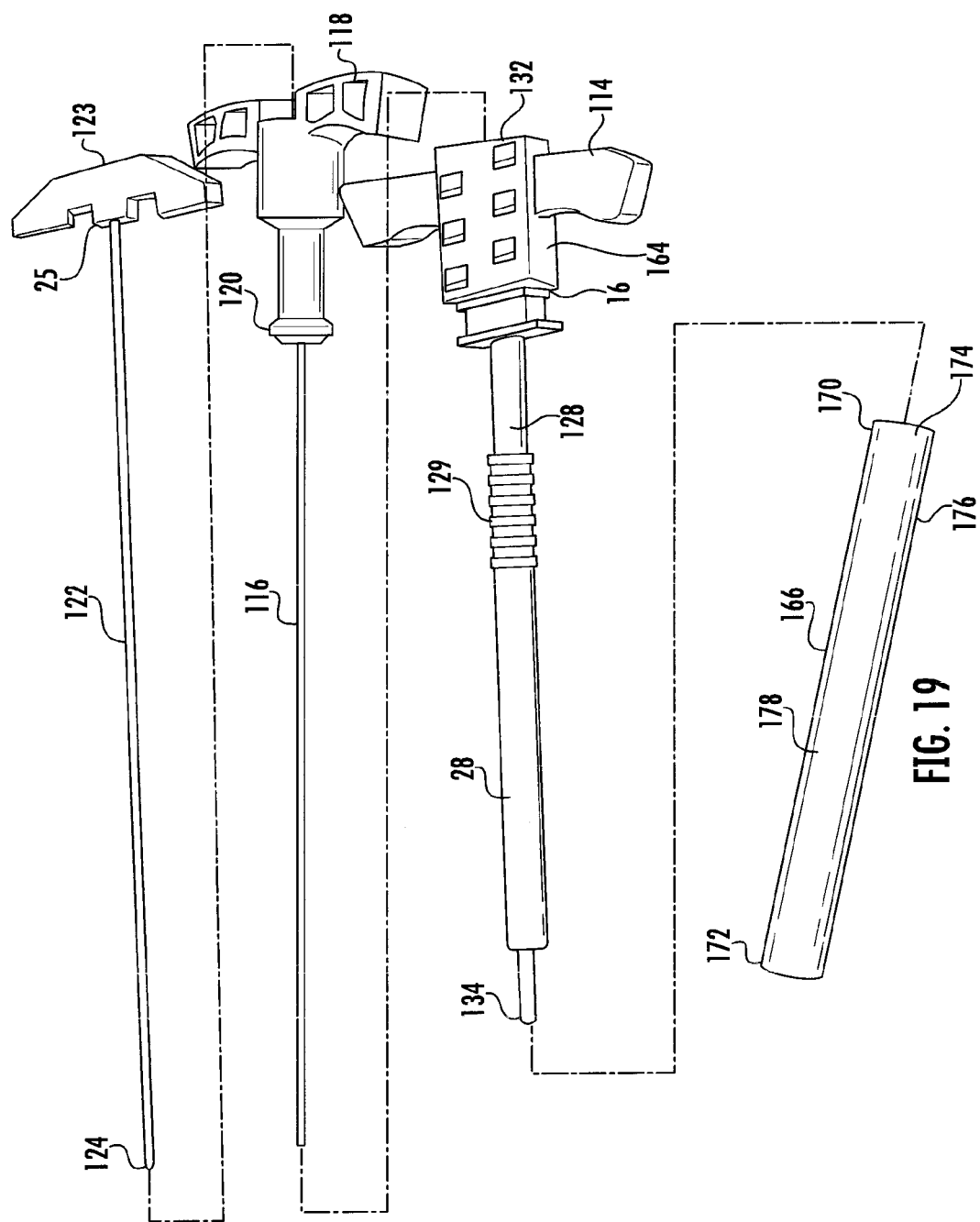
FIG. 19 is an exploded perspective view of the embodiment illustrated in FIG. 16.

Now referring to FIGS. 12-15, an alternative embodiment of the depth controlled jamshidi is illustrated. This embodiment includes at least one dilator tube 166 positioned about the outer cannula 114. In a most preferred embodiment, a pair of dilation tubes in the form of a tap tube 168 and a dilation tube 166 is positioned about the outer cannula 114. The tap tube includes a first end 170, a second end 172, an inner diameter 174 and an outer diameter 176. The tap tube generally includes a length that is slightly shorter than the outer cannula. In this manner, the tap tube can function as a stop member for the outer cannula, whereby the progression of the outer cannula through bone is stopped when the second end 172 of the tap tube contacts the outer surface of the bone. The inner diameter 174 of the tap tube 168 is sized to allow passage of a drill or tap member (not shown), thus the inner diameter also allows the tap tube to over the outer surface of the outer cannula. The first end 170 of the tap tube 168 preferably includes a connection to the outer cannula illustrated herein as internal threads 178 (FIG. 15). The second end 172 of the tap tube 168 is preferably tapered or radiused to allow for traversal through tissue in vivo. Thus, in operation, a surgeon can tap the depth controlled jamshidi needle 10 into a position wherein the second end 172 of the tap tube 168 contacts the bone. The surgeon can then rotate the handle 118 until the inner cannula 116 reaches the desired depth. The cap 123 of the needle 22 can be rotated to release the needle from the inner cannula 116. The needle is then withdrawn and a guidewire can be passed through funnel 17 and the inner cannula to the surgical site. The tap tube 168 can then be rotated to release it from the outer cannula 114. Gripping surface 178 provides the surgeon with sufficient friction to allow the tap tube to be released from the outer cannula. While the gripping surface 178 is illustrated as a knurled surface, other grippable surfaces may be utilized without departing from the scope of the invention; such gripping surfaces may include, but should not be limited to, wrench flats, an enlarged diameter, polygons and the like. The dilation tube 166 may be utilized in some embodiments over the outer diameter of the tap tube 168. The dilation tube includes a first end 180, a second end 182, an inner diameter 184 and an outer diameter 186. The first end 180 includes an attachment, illustrated herein as external threads 188 (FIG. 15) for attachment to the outer cannula. This construction allows the dilation tube 166 to be released as desired by the surgeon to leave the dilation tube in place. It should also be noted that while threads are illustrated, other types of attachments may be utilized without departing from the scope of the invention; such attachments may include, but should not be limited to, adhesives, friction, thumbscrews, locking tapers, and the like. The inner bore of the dilation tube 166 is sized to cooperate with the tap tube 168 and may be sized for passage of an implant such as a pedicle screw or the like. The second end of the dilation tube is preferably tapered or radiused to allow traversal through tissue in vivo. The tap tube 168 and the dilation tube 166 are preferably constructed from a polymeric plastic material. However, it should be noted that metals, rubbers and suitable combinations thereof may be utilized without departing from the scope of the invention.

FIGS. 16-19 illustrate an alternate embodiment of the present invention. In these figures, a Jamshidi-type assembly 112 is slidably disposed within an outer cannula assembly 114. The Janshidi-type needle assembly 112 includes a cannula 116 which is secured to a handle 118. The handle 118 includes a threaded collar portion 120. This threaded collar portion 120 is fixedly secured or molded to the handle 118. The handle 118 preferably has an ergonomic shape that can comfortably fit into a surgeon's or medical technician's hand. The handle includes an upper curved portion 115 which is shaped to conform to an individual's palm. The lower portion 117 of the handle 118 is also curved. The curve of the lower portion 117 of the handle is designed to be grasped by the fingers of an individual to assist in the control of the Jamshidi-type assembly 112. The handle 118 is used to drive the cannula into, and sometimes through bones of a vertebra. Sometimes the Jamshidi-type assembly 112 can be driven through the bone only by using pressure exerted by an individual's hand. Other times a hammer or other instrument must be employed to drive the Jamshidi-type assembly 112 through a bone. There is a risk, that when a hammer or similar instrument is utilized, the Jamshidi-type assembly 112 will pass too far into a vertebra. This can cause damage to nerves located nearby. Sometimes the needle passes completely through the vertebra and injures an adjacent blood vessel or internal organ. To prevent this, the present invention utilizes a second cannula 114 which is adjustably secured to the Jamshidi-type assembly 112 so that the Jamshidi assembly can pass through the second cannula assembly 114 in a precisely controlled manner once the second cannula assembly is embedded into the desired bone for anchoring.

A needle 122 is slidably positioned within the cannula 116. The needle, like the other embodiments includes an enlarged head member 123 which includes a boss 25 (FIG. 21) threads or the like suitable to secure the needle 122 within the cannula 116. In a most preferred embodiment, the boss 25 cooperates with the handle 118 to function as a bayonet type mount. This embodiment of the present invention illustrates the needle as having a conical tip 124, however, other tips and needles can also be employed. For example, a trocar needle or point formed from a plurality of flat surfaces etc. can be utilized. The tip 124 can be solid, tapered, hollow, etc. The tip can be utilized to extract a tissue sample. It can also be utilized to anchor the needle to a bone. A drill, tap and/or orthopedic bone screw or other device (not shown) can then be passed down the needle and secured to the correct location on a bone. While the preferred embodiment of the present invention discloses a relatively rigid needle, other needles which are flexible can also be employed. Alternatively, the bayonet mount may be utilized to remove the needle from the inner cannula for placement of a guidewire, K-wire or a Kirschner wire.

The outer cannula 114 comprises an upper portion 126 secured to a cannula 128 (FIG. 8). The upper portion 126 comprises a handle or grip 130. In this embodiment, the outer or second cannula 114 and the handle 130 are fixedly secured to each other. In other embodiments, these elements can be pivotably secured to each other. The lower end 134 of the outer cannula 114 is constructed and arranged to penetrate and pass through bone. While the end 134 is normally a hollow tube with an end that tapers to a sharp edge, other edges can also be employed. For example, the edge can be serrated, saw toothed or sinusoidal. The smooth edge is preferably utilized when the needle assembly is driven straight into or through a bone. The serrations or waves are employed when additional effort is required to penetrate a bone or tissue.

The Jamshidi-type assembly 112 of this embodiment includes a threaded collar portion 120. The second cannula 114 includes a housing 132 at a top end thereof. The housing is relatively hollow and includes internal threads which match the external threads on sleeve portion 120. After the surgeon inserts the needle into a patient and through the cortical bone 36 of a vertebra (FIG. 7), the cannula 116 is inserted further into the vertebra by rotating the handle 118 and sleeve portion 120. Rotation of sleeve 120 moves the cannula 116 and needle further into the vertebra. The distance that these elements are moved can be measured along the sleeve portion 120 which is provided with windows 162 and/or indicia 164. The distance the needle needs to travel into the vertebra, which has been determined by radiography, will be measured along sleeve portion 120. The surgeon or medical technician can now rotate handle 118 and sleeve 120 until it reaches the desired mark of indicia on sleeve 120. At this point, the cannula 116 and Jamshidi-type assembly 112 are now exactly where they need to be positioned.

Still referring to FIGS. 16-19, the preferred embodiment of the present invention incudes at least one tap tube 168 positioned about the outer cannula 114. In a most preferred embodiment, the tap tube 168 is positioned about the stop member 28 of the outer cannula 114. The stop member 28 is preferably molded around the outer cannula 128 however, press fits, shrink fits, adhesives, fasteners and the like may also be utilized to secure the stop member in place without departing from the scope of the invention. In a most preferred embodiment, threads 129 are formed into the stop member for threaded cooperation with the tap tube 166. The tap tube includes a first end 170, a second end 172, an inner diameter 174 and an outer diameter 176. The tap tube generally includes a length that is slightly shorter than the outer cannula 128. In this manner, the tap tube or the stop member can function as a stop member for the outer cannula, whereby the progression of the outer cannula through bone is stopped when the second end 172 of the tap tube or distal end of the stop member contacts the outer surface of the bone. The inner diameter 174 of the tap tube 168 includes threads sized to cooperate with the threads on the stop member and is sized to allow passage of a drill or tap member (not shown). The second end 172 of the tap tube 168 is preferably tapered or radiused to allow for traversal through tissue in vivo. Thus, in operation, a surgeon can tap the depth controlled jamshidi needle 10 into a position wherein the second end 172 of the tap tube 168 contacts the bone. The surgeon can then rotate the handle 118 until the inner cannula 116 reaches the desired depth. The cap 123 of the needle 22 can be rotated to release the needle from the inner cannula 116. The needle is then withdrawn and a guidewire can be passed through funnel 17 and the inner cannula to the surgical site. The tap tube 168 can then be rotated to release it from the outer cannula 114 and for backing the outer cannula out of the bone while leaving the tap tube in position. Gripping surface 178 provides the surgeon with sufficient friction to allow the tap tube to be released from the outer cannula. While the gripping surface 178 is illustrated as a knurled surface, other grippable surfaces may be utilized without departing from the scope of the invention; such gripping surfaces may include, but should not be limited to, wrench flats, an enlarged diameter, polygons and the like. A dilation tube 166 may be utilized in some embodiments over the outer diameter of the tap tube 168. The dilation tube includes a first end 180, a second end 182, an inner diameter 184 and an outer diameter 186. The first end 180 includes an attachment, illustrated herein as external threads 188 (FIG. 15) for attachment to the outer cannula. This construction allows the dilation tube 166 to be released as desired by the surgeon to leave the dilation tube in place. It should also be noted that while threads are illustrated, other types of attachments may be utilized without departing from the scope of the invention; such attachments may include, but should not be limited to, adhesives, friction, thumbscrews, locking tapers, and the like. The inner bore of the dilation tube 166 is sized to cooperate with the tap tube 168 and may be sized for passage of an implant such as a pedicle screw or the like. The second end of the dilation tube is preferably tapered or radiused to allow traversal through tissue in vivo. The tap tube 168 and the dilation tube 166 are preferably constructed from a polymeric plastic material. However, it should be noted that metals, rubbers and suitable combinations thereof may be utilized without departing from the scope of the invention.

Figure 20:
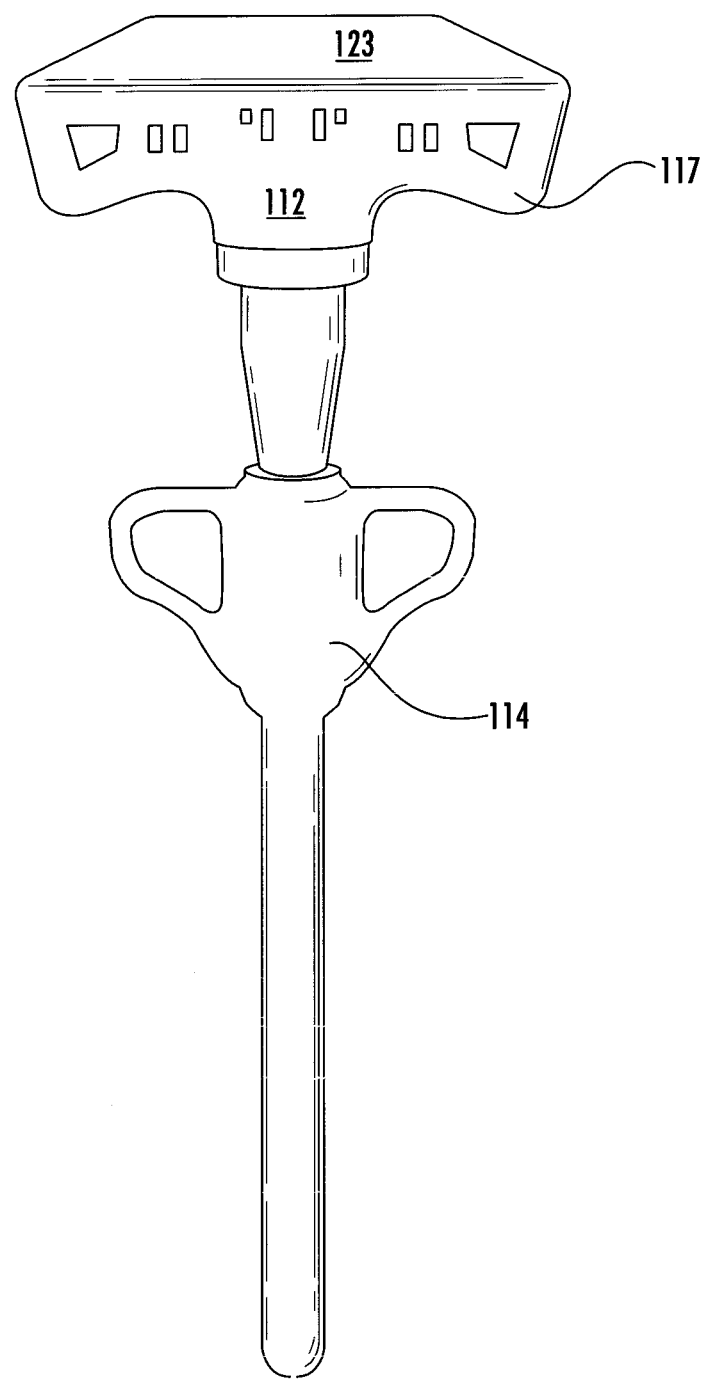
FIG. 20 is a perspective view of one embodiment of the present invention.
Figure 21:
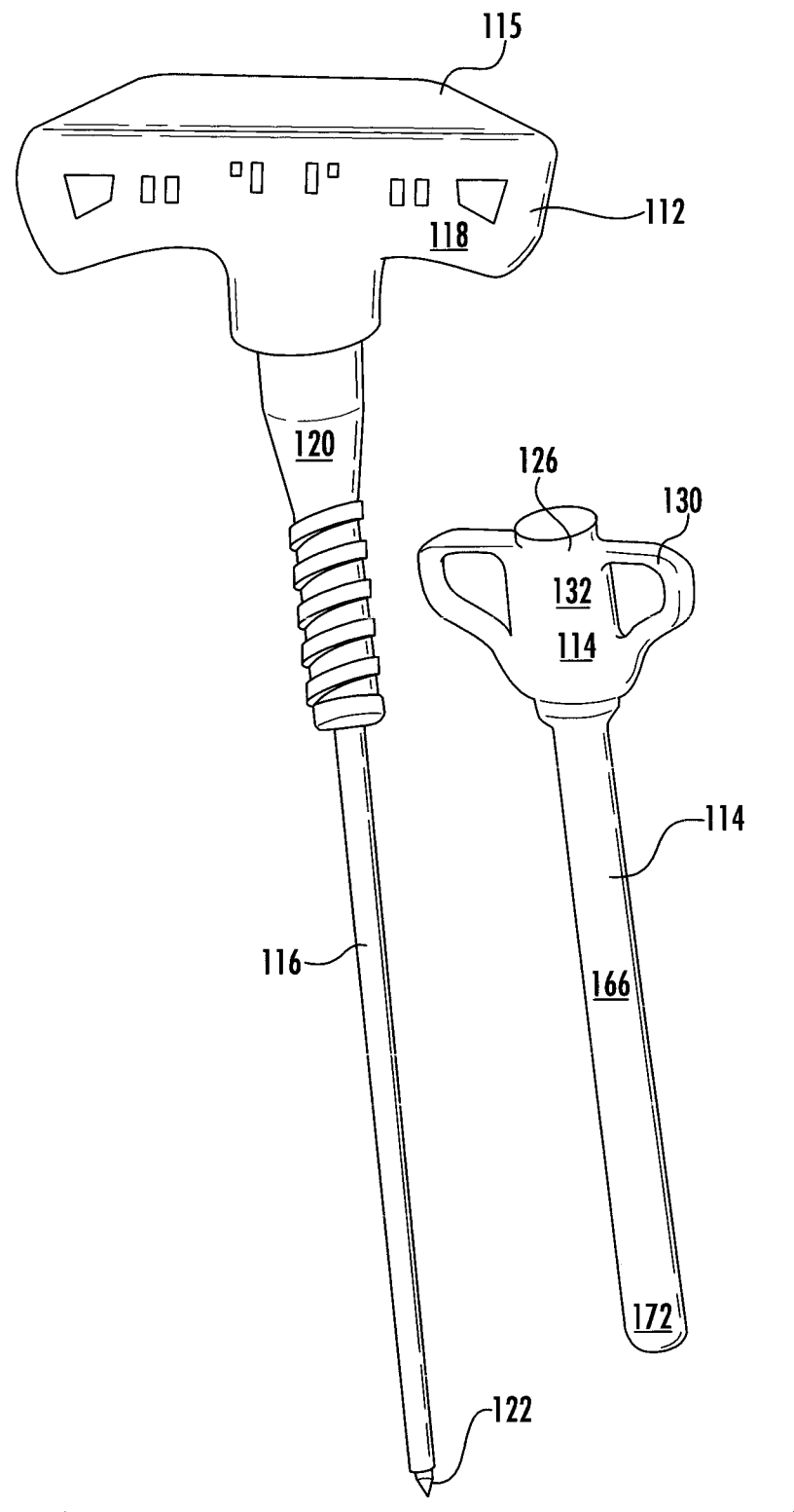
FIG. 21 is a partially exploded view of the embodiment illustrated in FIG. 19.

Referring to FIGS. 20-21, an alternative embodiment of the present invention is illustrated. In these figures, a Jamshidi-type assembly 112 is slidably disposed within an outer cannula assembly 114. The Jamshidi-type needle assembly 112 includes a cannula 116 which is secured to a handle 118. The handle 118 includes a threaded collar portion 120. This threaded collar portion 120 is fixedly secured or molded to the handle 118. The handle 118 preferably has an ergonomic shape that can comfortably fit into a surgeon's or medical technician's hand. The handle includes an upper curved portion 115 which is shaped to conform to an individual's palm. The lower portion 117 of the handle 118 is also curved. The curve of the lower portion 117 of the handle is designed to be grasped by the fingers of an individual to assist in the control of the Jamshidi-type assembly 112. The handle 118 is used to drive the cannula into, and sometimes through bones of a vertebra. Sometimes the Jamshidi-type assembly 112 can be driven through the bone only by using pressure exerted by an individual's hand. Other times a hammer or other instrument must be employed to drive the Jamshidi-type assembly 112 through a bone. There is a risk, that when a hammer or similar instrument is utilized, the Jamshidi-type assembly 112 will pass too far into a vertebra. This can cause damage to nerves located nearby. Sometimes the needle passes completely through the vertebra and injures an adjacent blood vessel or internal organ. To prevent this, the present invention utilizes a second cannula 114 which is adjustably secured to the Jamshidi-type assembly 112 via the threaded collar portion 120 so that the Jamshidi assembly can pass through the second cannula assembly 114 in a precisely controlled manner once the second cannula assembly is abutted to the desired bone for anchoring. Alternatively, the cannula 116 may be extended past a tap tube portion 166 of the second cannula 114 before be driven into the bone to limit the distance that the cannula 116 can penetrate the bone. Once the distal end 175 of the tap tube contacts the bone traversal of the cannula through the bone is stopped. Rotation of the jamshidi assembly in a first direction will cause further progression of the needle 122 through the bone or tissue while rotation in a second direction will pull the jamshidi assembly from the bone leaving the tap tube in position over the aperture created in the bone by the needle 122 and cannula 116.

A needle 122 is slidably positioned within the cannula 116. The needle, like the other embodiments includes an enlarged head member 123 which includes a boss 25 (FIG. 21) threads or the like suitable to secure the needle 122 within the cannula 116. In a most preferred embodiment, the boss 25 cooperates with the handle 118 to function as a bayonet type mount. This embodiment of the present invention illustrates the needle as having a conical tip 124, however, other tips and needles can also be employed. For example, a trocar needle or point formed from a plurality of flat surfaces etc. can be utilized. The tip 124 can be solid, tapered, hollow, etc. The tip can be utilized to extract a tissue sample. It can also be utilized to anchor the needle to a bone. A drill, tap and/or orthopedic bone screw or other device (not shown) can then be passed down the needle and secured to the correct location on a bone. While the preferred embodiment of the present invention discloses a relatively rigid needle, other needles which are flexible can also be employed. Alternatively, the bayonet mount may be utilized to remove the needle from the inner cannula for placement of a guidewire, K-wire or a Kirschner wire.

The outer cannula 114 comprises an upper portion 126 secured to a cannula 128 (FIG. 20). The upper portion 126 comprises a handle or grip 130. In this embodiment, the outer or second cannula 114 and the handle 130 are fixedly secured to each other. In other embodiments, these elements can be pivotably secured to each other. The lower end 134 of the outer cannula 114 is constructed and arranged to function as a tap tube 166 having an inner bore sized for the traversal of a tap member or drill bit (not shown) for sizing the aperture in the bone and/or forming threads therein for cooperation with a bone fastener (not shown).

The Jamshidi-type assembly 112 of this embodiment includes a threaded collar portion 120. The second cannula 114 includes a housing 132 at a top end thereof The housing is relatively hollow and includes internal threads which match the external threads on sleeve portion 120. After the surgeon inserts the needle into a patient and through the cortical bone 36 of a vertebra (FIG. 7), the cannula 116 is inserted further into the vertebra by rotating the handle 118 and sleeve portion 120. Rotation of sleeve 120 moves the cannula 116 and needle further into the vertebra. The distance that these elements are moved can be measured along the sleeve portion 120 which may be provided with windows and/or indicia.

Still referring to FIGS. 20-21, the preferred embodiment of the present invention incudes at least one tap tube 168 positioned about the outer cannula 114. In a most preferred embodiment, the tap tube 168 is positioned to function as a stop member to prevent over insertion of the jamshidi assembly. In this manner, the tap tube can function as a stop member for the outer cannula, whereby the progression of the outer cannula through bone is stopped when the second end 172 of the tap tube or distal end of the stop member contacts the outer surface of the bone. The inner diameter 174 of the tap tube 168 is sized to allow passage of a drill or tap member (not shown). The second end 172 of the tap tube 168 is preferably tapered or radiused to allow for traversal through tissue in vivo. Thus, in operation, a surgeon can tap the depth controlled jamshidi needle 10 into a position wherein the second end 172 of the tap tube 168 contacts the bone. The surgeon can then rotate the handle 118 until the inner cannula 116 reaches the desired depth. The cap 123 of the needle 22 can be rotated to release the needle from the inner cannula 116. The needle is then withdrawn and a guidewire can be passed through funnel 17 and the inner cannula to the surgical site. The tap tube 168 can then be rotated to release it from the outer cannula 114 and for backing the inner cannula out of the bone while leaving the tap tube in position. Gripping surface 130 provides the surgeon with sufficient friction to allow the tap tube to be released from the inner cannula. While the gripping surface 178 is illustrated as a handle 130, other grippable surfaces may be utilized without departing from the scope of the invention; such gripping surfaces may include, but should not be limited to, wrench flats, an enlarged diameter, polygons and the like. A dilation tube 166 (FIG. 14) may be utilized in some embodiments over the outer diameter of the tap tube 168. The dilation tube includes a first end 180, a second end 182, an inner diameter 184 and an outer diameter 186. The first end 180 includes an attachment, illustrated herein as external threads 188 (FIG. 15) for attachment to the outer cannula. This construction allows the dilation tube 166 to be released as desired by the surgeon to leave the dilation tube in place. It should also be noted that while threads are illustrated, other types of attachments may be utilized without departing from the scope of the invention; such attachments may include, but should not be limited to, adhesives, friction, thumbscrews, locking tapers, and the like. The inner bore of the dilation tube 166 is sized to cooperate with the tap tube 168 and may be sized for passage of an implant such as a pedicle screw or the like. The second end of the dilation tube is preferably tapered or radiused to allow traversal through tissue in vivo. The tap tube 168 and the dilation tube 166 are preferably constructed from a polymeric plastic material. However, it should be noted that metals, rubbers and suitable combinations thereof may be utilized without departing from the scope of the invention.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A jamshidi assembly comprising:
   an outer cannula assembly having a first portion of a depth controlling assembly secured thereto, said outer cannula assembly having a first stop member a predetermined distance from a distal end of said outer cannula assembly, said first stop member having a cylinder with a substantially same outer diameter across the length of the cylinder, said distal end of said outer cannula assembly constructed and arranged to penetrate a bone member a predetermined depth corresponding to said predetermined distance of said first stop member, said first stop member constructed and arranged to stop said outer cannula assembly from penetrating said bone member more than said predetermined depth,
   an inner cannula member removably secured within said outer cannula assembly, said inner cannula member secured to a second portion of a depth controlling assembly,
   a needle member removably secured within said inner cannula member so that a point portion of said needle member extends beyond the distal end of said inner cannula member,
   said first and said second portions of said depth controlling assembly cooperating to provide user controlled depth of penetration of said needle member and said inner cannula member into said bone, said inner cannula member and said needle member extending beyond said distal end of said outer cannula assembly, wherein said outer cannula assembly includes a tap tube positioned around said first stop member, said tap tube having an inner diameter sized to pass a helical thread tap member, said tap tube being removably secured to said outer cannula assembly.

2. The jamshidi assembly of claim 1, wherein the jamshidi assembly includes a dilation tube positioned around said tap tube, said dilation tube having an inner diameter sized to cooperate with said tap tube, said dilation tube removably secured to said outer cannula assembly.

3. The jamshidi assembly of claim 1, wherein said depth controlling assembly includes cooperating helical threads whereby rotation of said inner cannula member with respect to said outer cannula member provides synchronous linear traversal of said inner cannula member and said needle member with respect to said outer cannula member for control of said depth of penetration of said needle member and said inner cannula member into said bone.

4. The jamshidi assembly of claim 3 wherein said inner cannula member includes a handle member, said handle member including an internally disposed first of the cooperating helical threads, said first helical thread of the cooperating helical threads adapted to cooperate with a second cooperating helical thread of the cooperating helical threads of said outer cannula member to define said depth controlling assembly.

5. The jamshidi assembly of claim 4, wherein said outer cannula member includes a handle member, said handle member including said second helical thread of the cooperating helical threads, said second cooperating helical thread being externally disposed and adapted to cooperate with said first helical thread of said inner cannula member.

* * * * *